United States Patent
Brown et al.

(10) Patent No.: US 9,694,106 B2
(45) Date of Patent: Jul. 4, 2017

(54) SYNTHETIC COLLAGEN THREADS FOR COSMETIC USES INCLUDING SKIN WRINKLE TREATMENTS AND ASSOCIATED METHODS

(75) Inventors: Rebeccah Brown, Decatur, GA (US); Thomas J. Koob, Tampa, FL (US)

(73) Assignee: MiMedx Group, Inc., Marietta, GA (US)

( * ) Notice: Subject to any disclaimer, the term of this patent is extended or adjusted under 35 U.S.C. 154(b) by 166 days.

(21) Appl. No.: 13/545,235

(22) Filed: Jul. 10, 2012

(65) Prior Publication Data

US 2013/0018415 A1 Jan. 17, 2013

Related U.S. Application Data

(60) Provisional application No. 61/506,302, filed on Jul. 11, 2011.

(51) Int. Cl.
*A61B 17/00* (2006.01)
*A61B 17/06* (2006.01)
*A61L 27/22* (2006.01)
*A61L 17/06* (2006.01)
*A61L 27/24* (2006.01)
*A61L 27/52* (2006.01)
*A61F 2/00* (2006.01)

(52) U.S. Cl.
CPC ........ *A61L 27/222* (2013.01); *A61B 17/0057* (2013.01); *A61B 17/06166* (2013.01); *A61L 17/06* (2013.01); *A61L 27/24* (2013.01); *A61L 27/52* (2013.01); *A61B 2017/00004* (2013.01); *A61B 2017/00654* (2013.01); *A61B 2017/00792* (2013.01); *A61B 2017/00898* (2013.01); *A61F 2/0059* (2013.01); *A61L 2430/34* (2013.01)

(58) Field of Classification Search
CPC A61B 2017/00663; A61B 2017/00792; A61B 19/24; A61B 17/06; A61B 17/0057; A61B 17/04; A61B 2017/00004; A61B 17/06166; A61F 2/0059; A61F 2210/0061; A61F 2210/0004; A61L 27/24
USPC .................................................. 606/229, 224
See application file for complete search history.

(56) References Cited

U.S. PATENT DOCUMENTS

| | | | |
|---|---|---|---|
| 3,316,699 A | 5/1967 | Mattingly | |
| 4,451,397 A * | 5/1984 | Huc et al. | ..... 530/356 |

(Continued)

FOREIGN PATENT DOCUMENTS

| | | |
|---|---|---|
| CA | 2285161 | 4/2001 |
| EP | 1493404 | 1/2005 |

(Continued)

OTHER PUBLICATIONS

Hafemann et al., Cross-linking by 1-ethyl-3-(3-dimethylaminopropyl)-carbodiimide (EDC) of a collagen/elastin membrane meant to be used as a dermal substitute: effects on physical, biochemical and biological features in vitro, Journal of Materials Science: Materials in Medicine, 2001, pp. 437-446, vol. 12.

(Continued)

*Primary Examiner* — Tuan V Nguyen
*Assistant Examiner* — Chima Igboko
(74) *Attorney, Agent, or Firm* — Myers Bigel,, P.A.

(57) ABSTRACT

Cosmetic threads for reducing wrinkle size include at least one synthetic collagen fiber that wells after placement under the skin.

17 Claims, 4 Drawing Sheets

(56) References Cited

U.S. PATENT DOCUMENTS

| | | | |
|---|---|---|---|
| 4,590,928 A | | 5/1986 | Hunt et al. |
| 4,776,890 A | * | 10/1988 | Chu .................. 106/151.1 |
| 4,792,336 A | | 12/1988 | Hlavacek et al. |
| 4,841,962 A | | 6/1989 | Berg et al. |
| 4,883,486 A | | 11/1989 | Kapadia et al. |
| 4,970,298 A | * | 11/1990 | Silver .................. A61K 9/70 |
| | | | 128/DIG. 8 |
| 4,979,956 A | | 12/1990 | Silvestrini |
| 5,078,744 A | | 1/1992 | Chvapil |
| 5,106,949 A | | 4/1992 | Kemp et al. |
| 5,256,418 A | | 10/1993 | Kemp et al. |
| 5,263,984 A | | 11/1993 | Li et al. |
| 5,378,469 A | | 1/1995 | Kemp et al. |
| 5,656,605 A | | 8/1997 | Hansson et al. |
| 5,713,374 A | | 2/1998 | Pachence et al. |
| 5,718,012 A | | 2/1998 | Cavallaro |
| 5,718,717 A | | 2/1998 | Bonutti |
| 6,086,578 A | | 7/2000 | Adamyan et al. |
| 6,090,117 A | | 7/2000 | Shimizu |
| 6,224,630 B1 | | 5/2001 | Bao et al. |
| 6,277,397 B1 | | 8/2001 | Shimizu |
| 6,280,474 B1 | * | 8/2001 | Cassidy et al. ............ 623/16.11 |
| 6,292,697 B1 | | 9/2001 | Roberts |
| 6,335,007 B1 | | 1/2002 | Shimizu et al. |
| 6,531,147 B2 | | 3/2003 | Sawhney et al. |
| 6,565,960 B2 | | 5/2003 | Koob et al. |
| 6,589,257 B1 | | 7/2003 | Shimizu |
| 6,592,623 B1 | | 7/2003 | Bowlin et al. |
| 6,645,247 B2 | | 11/2003 | Ferree |
| 6,692,528 B2 | | 2/2004 | Ward et al. |
| 6,713,537 B1 | | 3/2004 | Ueda et al. |
| 6,730,124 B2 | | 5/2004 | Steiner |
| 6,752,831 B2 | | 6/2004 | Sybert et al. |
| 6,821,530 B2 | | 11/2004 | Koob et al. |
| 6,936,072 B2 | | 8/2005 | Lambrecht et al. |
| 6,955,683 B2 | | 10/2005 | Bonutti |
| 7,084,082 B1 | | 8/2006 | Shimizu |
| 7,090,690 B2 | | 8/2006 | Foerster et al. |
| 7,115,146 B2 | | 10/2006 | Boyer et al. |
| 7,135,040 B2 | | 11/2006 | Wang et al. |
| 7,309,359 B2 | | 12/2007 | Trieu et al. |
| 7,354,627 B2 | | 4/2008 | Pedrozo et al. |
| 7,513,904 B2 | * | 4/2009 | Sulamanidze et al. ....... 606/224 |
| 8,470,356 B2 | * | 6/2013 | Patel et al. .................... 424/423 |
| 2001/0018619 A1 | | 8/2001 | Enzerink et al. |
| 2002/0037940 A1 | | 3/2002 | Koob et al. |
| 2002/0123805 A1 | | 9/2002 | Murray et al. |
| 2003/0100108 A1 | | 5/2003 | Altman et al. |
| 2003/0230316 A1 | | 12/2003 | Glucksman et al. |
| 2004/0110439 A1 | * | 6/2004 | Chaikof .................. A61L 15/32 |
| | | | 442/123 |
| 2004/0131562 A1 | | 7/2004 | Gower et al. |
| 2004/0193241 A1 | | 9/2004 | Stinson |
| 2004/0224406 A1 | | 11/2004 | Altman et al. |
| 2004/0267362 A1 | | 12/2004 | Hwang et al. |
| 2006/0095134 A1 | | 5/2006 | Trieu et al. |
| 2006/0161253 A1 | * | 7/2006 | Lesh ................................. 623/8 |
| 2006/0257377 A1 | | 11/2006 | Atala et al. |
| 2006/0263417 A1 | | 11/2006 | Lelkes et al. |
| 2007/0020225 A1 | * | 1/2007 | Abramson et al. ......... 424/78.27 |
| 2007/0067045 A1 | * | 3/2007 | Phan .......................... A61F 2/02 |
| | | | 623/23.72 |
| 2007/0098755 A1 | * | 5/2007 | Patel et al. .................... 424/423 |
| 2007/0118217 A1 | | 5/2007 | Brulez et al. |
| 2007/0248643 A1 | | 10/2007 | Devore et al. |
| 2007/0280990 A1 | * | 12/2007 | Stopek .......................... 424/423 |
| 2008/0020012 A1 | | 1/2008 | Ju et al. |
| 2008/0038352 A1 | | 2/2008 | Simpson et al. |
| 2008/0124371 A1 | | 5/2008 | Turos et al. |
| 2008/0161917 A1 | | 7/2008 | Koob et al. |
| 2008/0188933 A1 | * | 8/2008 | Koob et al. ................. 623/13.12 |
| 2008/0200992 A1 | * | 8/2008 | Koob et al. ................. 623/23.72 |
| 2008/0215150 A1 | | 9/2008 | Koob et al. |
| 2008/0294193 A1 | * | 11/2008 | Schwartz et al. ............. 606/228 |
| 2009/0216233 A1 | | 8/2009 | Wiedrich et al. |
| 2009/0222039 A1 | * | 9/2009 | Dreyfuss et al. ............. 606/229 |
| 2009/0234384 A1 | * | 9/2009 | Hadba .............. A61B 17/06166 |
| | | | 606/215 |
| 2009/0287308 A1 | * | 11/2009 | Davis et al. ................ 623/13.12 |
| 2011/0257581 A1 | * | 10/2011 | Koziczynski et al. .......... 604/11 |

FOREIGN PATENT DOCUMENTS

| | | |
|---|---|---|
| WO | WO 96-14095 | 5/1996 |
| WO | WO 01-72241 | 10/2001 |
| WO | WO 2008-041183 | 4/2008 |

OTHER PUBLICATIONS

Koob et al., Mechanical and thermal properties of novel polymerized NDGA-gelatin hydrogels, Biomaterials, vol. 24, 2003, pp. 1285-1292.

Koob, Thomas J., Biomimetic approaches to tendon repair, Comparative Biochemistry and Physiology, Part A, vol. 133, 2002, pp. 1171-1192.

Brunelli et al., Slip-knot flexor tendon suture in zone II allowing immediate mobilisation, The Hand, 1983, vol. 15, pp. 352-358.

Greis et al, "The influence of tendon length and fit on the strength of the tendon-bone tunnel complex", Am. J. Sports Med., 2001, 29:493-497.

Becker et al., Early active motion following a beveled technique of flexor tendon repair: Report on fifty cases, Journal of Hand Surgery, 1979, vol. 4 No. 5, pp. 454-460.

Frantz et al., "The extracellular matrix at a glance", Journal of Cell Science, 2010, 123: 4195-4200.

Grog, The Reef (Square) Knot, Animated Knots by Grog, downloaded at http://www.animatedknots.com/reef/index.php, on May 28, 2009 using WayBack Machine on www.archive.org for publication date of Dec. 26, 2005.

Kakisis, J., et al., Artificial blood vessel: The Holy Grail of peripheral vascular surgery, Journal of Vascular Surgery, vol. 41, Issue 2, 2003, pp. 349-354.

Koob et al., Biocompatibility of NDGA-polymerized collagen fibers. II. Attachment, proliferation, and migration of tendon fibroblasts in vitro, © 2001John Wile & Sons, Inc.

Martin et al., Anterior Cruciate Ligament Graft Preparation: A New and Quick Alternative to the Whipstitch, Arthroscopy: The Journal of Arthroscopic & Related Surgery, Online Publication Date of Nov. 29, 2006.

Messina, The double armed suture: Tendon repair with immediate mobilization of the fingers, Journal of Hand Surgery, 1992, 17A:137-142.

Nottage et al., Arthoscopic Knot Tying Techniques, Arthroscopy: The Journal of Arthroscopic & Related Surgery 15(1999): 515-521.

Powell et al., Forces transmitted along human flexor tendons during passive and active movements of the fingers, J. Hand Surg., 2004, 29:4:386-389.

Rodeo et al., Tendon healing in a bone tunnel. A biomechanical and histological study in a dog, J. Bone Joint Surg., 1993, 75:1795-1803.

Savage et al., Flexor tendon repair using a "six strand" method of repair and early active mobilisation, Journal of Hand Surgery, (British vol. 1989), 14B:396-399.

Silva et al., The insertion site of the canine flexor digitorum profundus tendon heals slowly following injury and suture repair, J. Orthop. Res., 2002, 20:447-453.

Trotter et al., Molecular structure and functional morphology of echinoderm collagen fibrils, Cell Tiss. Res., 1994, 275: 451-458.

Product advertisement, Conair QB3ECS Quick Braid Styling Kit, © (1 page).

Integra™ NeuraGen™ Nerve Guide, Product Brochure, 4 pages 2005.

Integra™ NeuraGen™ Nerve Guide, Product Webpage, http://www.integra-Is.com/products/?product=88, Date unknown but believed to be prior to the filing date of the present application, 2 pages.

(56) References Cited

OTHER PUBLICATIONS

Integra™ NeuraWrap™ Nerve Protector, Product Webpage, http://www.integra-ls.com/products/?product=198, Date unknown but believed to be prior to the filing date of the present application, 2 pages.

Biosingularity, Advances in biological systems, Google Ad, MIT Technology Review, 2006, 1 Page.

* cited by examiner

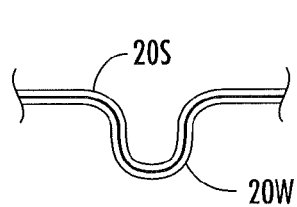 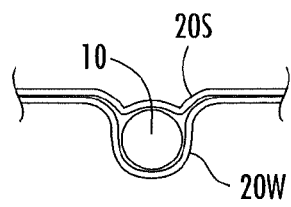 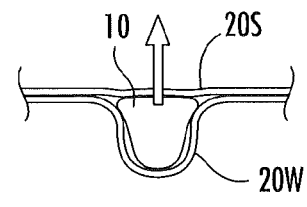
FIG. 5A  FIG. 5B  FIG. 5C
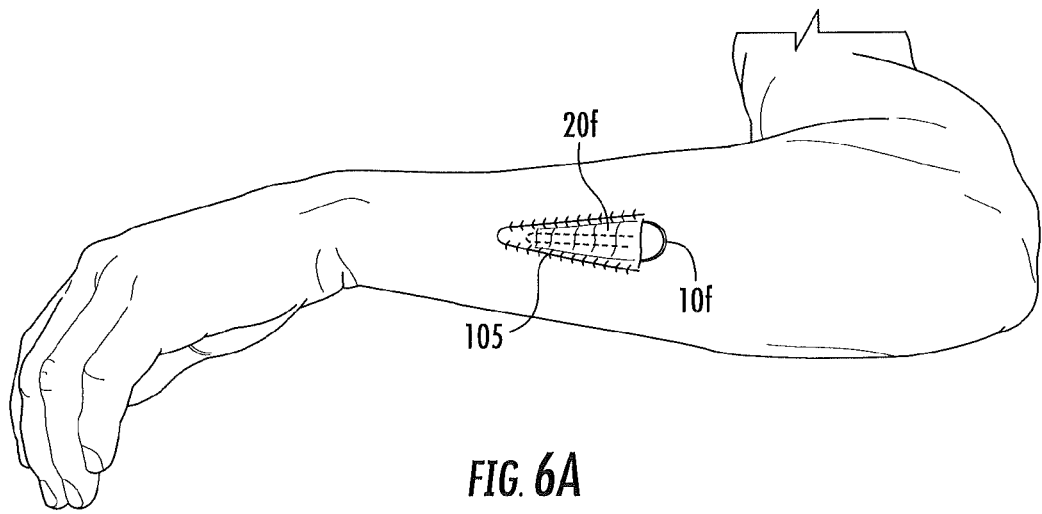
FIG. 6A
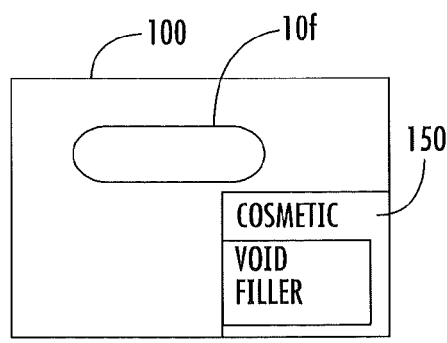
FIG. 6B SYNTHETIC COLLAGEN THREADS FOR COSMETIC USES INCLUDING SKIN WRINKLE TREATMENTS AND ASSOCIATED METHODS

RELATED APPLICATIONS

This application claims the benefit of and priority to U.S. Provisional Application Ser. No. 61/506,302, filed Jul. 11, 2011, the contents of which are hereby incorporated by reference as if recited in full herein.

FIELD OF THE INVENTION

The invention relates to cosmetic treatments.

BACKGROUND OF THE INVENTION

External lotions and creams, laser treatments and BOTOX® injections have all been proposed for reducing wrinkles due to aging and/or skin exposure. Despite the above, there remains a need for alternative treatment options.

SUMMARY OF EMBODIMENTS OF THE INVENTION

Embodiments of the invention are directed to threads of at least one elongate synthetic collagen fiber for cosmetic uses.

Embodiments of the invention are directed to methods of placing at least one thread of at least one synthetic collagen fiber under an outer layer of skin for treating cosmetic conditions such as wrinkles, scars, tissue voids or other externally visible features.

The thread with the at least one collagen fiber can be configured to swell from a non-hydrated or partially hydrated state to a fully hydrated state, which may occur in about 10 minutes to about 48 hours after placement. The thread may swell (in lateral cross-section), by at least about 30%, typically between about 30% to about 500% (and even greater for certain gelatin hydrogel threads).

The thread with the at least one elongate synthetic collagen fiber can be placed under the outer layer of skin (e.g., the epithelium) in a subdermal location to fill a crevice or void (such as that associated with a wrinkle, or excised or otherwise missing or removed sub-surface tissue).

Embodiments of the invention are directed to medical threads for cosmetic uses. The threads include at least one synthetic collagen fiber having a length that is at least about 0.25 inches. The thread is implantable and provided in a dry or partially hydrated state.

The at least one thread can be configured to swell in situ in cross-sectional size at least about 30% after implantation and when fully hydrated, wherein the thread is degradable or resorbable in vivo.

The thread can be attached to a needle for placing the thread under an outer layer of skin of a patient. The thread can be sized and configured to reside in a tissue void associated with a wrinkle under an outer layer of skin and, when fully hydrated, is configured to push the outer layer of skin outward.

The thread can be sized and configured for placement in a facial wrinkle to reduce wrinkle size.

The thread can include a single synthetic collagen fiber having a diameter between about 0.01 mm to about 2 mm.

The thread can include a plurality of braided and/or twisted synthetic collagen fibers, and can have a diameter between about 0.1 mm to about 2 mm.

The thread can be defined by a single elongate gelatin hydrogel fiber having a diameter between about 0.1 mm to about 2 mm.

Still other embodiments are directed to a cosmetic treatment kit. The kit includes at least one thread comprising at least one synthetic collagen fiber in a dry or partially hydrated state.

The at least one thread can be a plurality of threads of different diameters for treating different size facial wrinkles.

The kit can include at least one needle sized and configured to insert a respective thread into tissue associated with a wrinkle.

The at least one thread can be configured to swell in situ in cross-sectional size at least about 30% after placement when fully hydrated.

The thread can be degradable or resorbable in vivo.

The at least one synthetic collagen fiber can be un-cross linked.

The at least one synthetic collagen fiber can be cross-linked.

Yet other embodiments are directed to methods of treating wrinkles or subdermal tissue voids. The methods include: (a) placing a dry or partially hydrated thread comprising at least one synthetic collagen fiber under an outer layer of skin; (b) hydrating the thread after the placing step to cause the thread to swell in cross-sectional size by at least about 30%; and (c) pushing the outer layer of skin outward in response to the hydrating step.

The placing step can be carried out using a needle attached to the thread. The needle can be inserted under the skin and used to pull a length of the thread into a wrinkle crevice under the outer layer of skin.

Other embodiments are directed to implantable soft tissue void fillers. The void filler can include a sterile package with at least one synthetic collagen fiber and/or gelatin hydrogel for implantation in a dry or partially hydrated state in the package. The at least one collagen fiber can have a length that is at least about 0.25 inches. The void filler is flexible and configured to reside under an outer skin layer to be able to lift the outer skin layer. The package can include a use label on or in the package identifying the at least one synthetic collagen fiber as a soft tissue void filler for cosmetic and/or non-structural purposes.

The void filler can be configured to swell in situ in cross-sectional size at least about 30% after implantation, when fully hydrated.

The void filler can include the gelatin hydrogel.

The void thread can be degradable or resorbable in vivo.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

Further features, advantages and details of the present invention will be appreciated by those of ordinary skill in the art from a reading of the figures and the detailed description of the embodiments that follow, such description being merely illustrative of the present invention.

BRIEF DESCRIPTION OF THE DRAWINGS

FIGS. 5A-5C are schematic partial cross-sectional views of a sequence of steps that can use threads to fill tissue voids, valleys or crevices (such as those associated with wrinkles) according to embodiments of the invention.

FIG. 6A is a schematic top view of a soft tissue void filler used to fill a tissue void according to other embodiments of the present invention. FIG. 6B is a schematic illustration of the void filler in a sterile package according to embodiments of the present invention.

DETAILED DESCRIPTION

Figure 1:
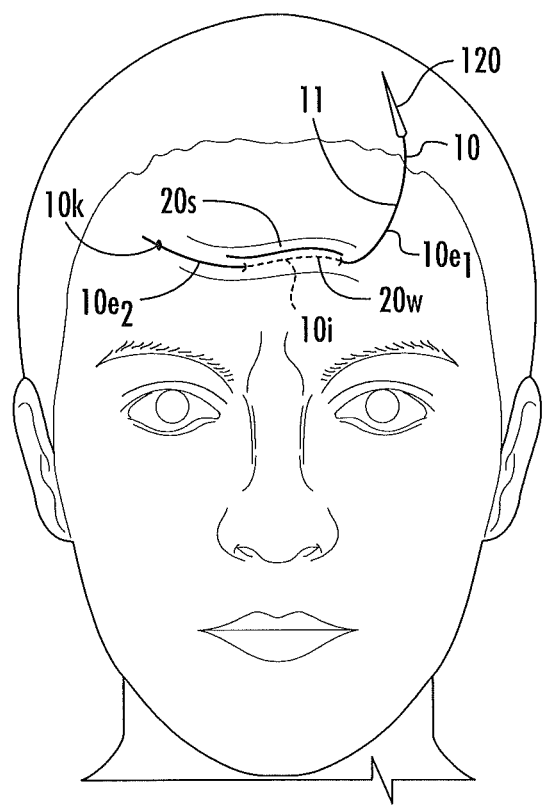
FIG. 1 is a schematic illustration of a cosmetic use of a thread comprising at least one synthetic collagen fiber according to embodiments of the present invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y." The term "about" means that the recited parameter (number) can vary between +/−20% from the noted value.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

The term "sterile" refers to a degree of cleanliness that meets or exceeds medical standards for patient safety (e.g., to be substantially free of germs and/or pathogens) such as those defined in applicable in the United States Food and Drug Administration rules, regulations or guidelines.

It will be understood that, although the terms first, second, etc, may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

Embodiments of the present invention comprise collagen, typically dermal collagen. However, the collagen can be of any form and from any origin. The collagen can be any of the identified collagen genotypes, for example, the interstitial fiber forming collagen types I, II and III, as well as any other substantially fiber forming types of collagen, for example collagen VI. The collagen can be acid soluble collagen or pepsin solubilized or soluble collagen. The collagen can be from mammalian cells synthesized in vitro. The collagen can be from molecularly engineered constructs and synthesized by bacterial, yeast or any other molecularly manipulated cell type. For example, the collagen can be sea cucumber dermis collagen, bovine, caprine, porcine, ovine or other suitable donor mammal, marine animal collagen such as chinoderms, molecularly engineered collagen, or gelatin (e.g., in any suitable form including solid, gel, hydrogels, liquids, or foams). In addition, the collagen can be digested with a protease before, where used, oxidizing and polymerizing steps. The collagen can be in the form of microfibrils, fibrils, natural fibers, or synthetic fibers.

In some embodiments, the collagen can be solubilized, dissolved or otherwise transferred into an acid solution, for example, acetic acid (e.g., about 0.01 M to about 1.0 M, typically about 0.5 M), hydrochloric acid (between about pH 1 to about pH 3, typically about pH 2.0), or any other suitable acid at appropriate concentration (e.g., about pH 1.0 to about pH 3.0, typically about pH 2.0). Dialysis may optionally be used to neutralize a soluble collagen solution. The collagen can also or alternatively be dissolved in a neutral buffered solution either with or without salts, e.g., phosphate buffer at about pH 7.0, or phosphate buffered saline at about pH 7.0. The phosphate buffer can be at any concentration of sodium phosphate between about 0.01 M and about 0.5 M, but more typically between about 0.02 M and about 0.1M. The buffer can also be any buffer, including, but not limited to, for example, sodium acetate, 4-(2-hydroxyethyl)-1-piperazineethanesulfonic acid (HEPES), or 3-(N-morpholino)propanesulfonic acid (MOPS). The collagen can be present in a quantity that is at least about 0.1% to about 10%, typically between about 0.1% to about 5% (e.g., about 0.1, 0.2, 0.3, 0.4, 1.0, 2.0, or 4.0%) weight per volume, or weight per volume in the neutral buffer solution before fibrillogenesis and fiber formation. In a dried fiber collagen, collagen can be present in an amount of weight by volume of between about 50-100% (e.g., at least about 75%, 90%, 95% or 100%) before crosslinking (where crosslinking is used).

Collagen "microfibrils," "fibrils," "fibers," and "natural fibers" refer to naturally-occurring structures found in a tendon. Microfibrils are about 3.5 to 50 nm in diameter. Fibrils are about 50 nm to 50 μm in diameter. Natural fibers are above 50 μm in diameter. A "synthetic fiber" refers to any fiber-like material that has been formed and/or chemically or physically created or altered from its naturally-occurring state. For example, an extruded gel of fibrils or a fiber of fibrils formed from a digested tendon is a synthetic fiber but a tendon fiber newly harvested from a mammal is a natural fiber. Of course, synthetic collagen fibers can include non-collagenous components, such as particulates, hydroxyapatite and other mineral phases, or drugs that facilitate tissue growth. See, U.S. Pat. No. 6,821,530, hereby incorporated by reference herein. For example, the compositions can contain carbon nano-tubes, zinc nano-wires, nano-crystalline diamond, or other nano-scale particulates, or larger crystalline and non-crystalline particulates such as calcium phosphate, calcium sulfate, and apatite minerals. For example, the fibers and/or constructs formed of the fibers can include compositions that contain therapeutic agents such as bisphosphonates, anti-inflammatory steroids, growth factors such as basic fibroblast growth factor, tumor growth factor beta, bone morphogenic proteins, platelet-derived growth factor, and insulin-like growth factors; chemotactic factors such fibronectin and hyaluronan; and extracellular matrix molecules such as aggrecan, biglycan, and decorin. In some embodiments, the fibers and/or constructs can contain cells, engineered cells, stem cells, and the like, as well as combinations of the above.

The term "gelatin" refers to denatured collagen. Gelatin can be derived from collagen in a well known manner or can be obtained from commercial suppliers, such as Sigma-Aldrich®, located in St. Louis, Mo. An exemplary method of obtaining gelatin is by heating collagen at a suitable temperature to cause it to become denatured. Denaturation results in the irreversible transformation of collagen into a random coiled structure, which is gelatin. Gelatin can be derived from one or more sources of collagen and derived from one or more types of collagen, such as but not limited to types I, II, III, and/or VI. Exemplary sources from which gelatin is derived include, but are not limited to, sea cucumber dermis collagen, bovine, caprine, porcine, ovine or other suitable donor mammal collagen, and marine animal collagen such as from chinoderms. The gelatin can be derived from collagen obtained from mammalian cells synthesized in vitro. The gelatin can be derived from collagen obtained from molecularly engineered constructs and synthesized by bacterial, yeast or any other molecularly manipulated cell type.

The term "gelatin hydrogel" as used herein refers to a semi-solid (e.g., gelatinous density) material formed by the gelatin slurry that includes gelatin and can comprise other components, such as, but not limited to, one or more minerals and/or particulates. The gelatin in the gelatin slurry and in the resulting gelatin hydrogel is composed of denatured collagen and cannot be used to produce collagen fibers, fibrils, and/or microfibrils. To be clear, in contrast, the term "collagen gel" as used herein refers to a gel that includes collagen fiber, fibrils and/or microfibrils that has been acid or pepsin solubilized (e.g., soluble collagen) and processed to maintain the collagen in its molecular form, whereas the terms "gelatin hydrogel" and "gelatin slurry" as used herein refer to compositions of gelatin, which is denatured collagen that cannot be used to produce collagen fibers, fibrils, and/or microfibrils. Stated differently, gelatin is denatured collagen which does not maintain collagen in its molecular form since it is irreversibly transformed into a random coiled structure.

The gelatin slurry and/or gelatin hydrogel can be stabilized with treatments, such as, but not limited to, one or more of dehydrothermal treatment, glycation, and ultraviolet light. The gelatin slurry and/or the gelatin hydrogel treated with a polymerizing material and/or a stabilization treatment can be resistant to liquification at 37° C. and/or thermally stable at temperatures over about 37° C. The gelatin slurry and/or the gelatin hydrogel treated with a polymerizing material and/or a stabilization treatment can be thermally stable at temperatures up to about 120° C., typically at temperatures between about 37° C. to about 104° C. The polymerized and/or stabilized gelatin hydrogel can be stronger and/or stiffer than an untreated gelatin slurry and/or gelatin hydrogel (e.g., an untreated gelatin hydrogel has a compressive stiffness of about 0.70 MPa, compared to about 4.71 MPa for NDGA-treated gelatin hydrogel). The polymerized and/or stabilized gelatin hydrogel can be nearly elastic under dynamic compression loads (e.g., rebounds substantially completely after compression to over 80%, while untreated gelatin hydrogels fracture when compressed to 80%). The polymerized and/or stabilized gelatin hydrogel can undergo large deformations without comprising its mechanical properties.

Generally stated, the skin can be described as having three primary layers: the external covering or epithelium (the outer layer is also called the epidermis), the dermis and the hypodermis. The epidermis is non-vascular, and consists of stratified epithelium. Embodiments of the invention contemplate placing the thread under the outer layer of the skin in a non-load bearing (cosmetic) manner such as in the epidermis, dermis or hypodermis, or even under the hypodermis but in a location that has an impact on external appearance of the overlying skin or tissue structure (e.g., a subdermal location).

The term "thread" refers to a relatively thin length of at least one synthetic collagen fiber and can include multiple synthetic collagen fibers. The thread can have a lateral cross-sectional size (e.g., diameter) of between about 0.01 mm to about 3 mm, average (dry), typically between about 0.1 mm to about 2 mm, average (dry). The thread can have length that is at least about 0.25 inches, typically at least about 0.5 inches, and more typically between about 1-30 inches. The synthetic collagen fiber can be an elongate continuous length of fiber formed of denatured (gelatin) or non-denatured collagen. The fiber, like the thread, has a length of least about 0.25 inches, typically greater than about 0.5 inches, and more typically between about 1-30 inches.

The term "implantable" means the thread can be inserted, injected, sewn, drawn, embedded, grafted or otherwise chronically placed under an external layer of skin of a patient for cosmetic (non-load bearing) uses. For example, an implanted thread can be placed under an outer layer of the skin and allowed to swell to reduce the appearance of wrinkles. A wrinkle is a fold, ridge or crease in the skin. Skin wrinkles typically appear as a result of aging processes or as the result of prolonged exposure to sun or immersion in water. Wrinkling in the skin can be caused by habitual facial expressions, aging, sun damage, smoking, poor hydration, and various other factors.

The term "dry" means the thread (fiber or fibers forming such thread) has a moisture content that is substantially less than the amount present when fully hydrated (e.g., at equilibrium). The term "partially hydrated" means that the thread and/or fibers thereof have a moisture content that is less than about 50%, typically less than about 75%, of the moisture content at full hydration, which can be measured ex vivo after about 24 hours in a saline bath at ambient conditions.

FIG. 1 illustrates that the synthetic collagen fiber thread 10 can be placed under the outer layer of skin 20s (e.g., the epithelium) to fill a crevice or void that may be associated with a wrinkle 20w, or excised or otherwise missing or removed sub-surface tissue. The thread 10 includes at least one elongate synthetic collagen fiber 11 and is typically placed in the epidermis or dermis layers, but may optionally be placed below the dermis such as in the hypodermis or even under the hypodermis, typically at a depth that can produce or cause a change in an externally visible feature of the skin or tissue as the thread/fiber swells after placemen, in situ. The thread 10 can be substantially dry at placement or partially hydrated. The thread 10 may be configured to fully hydrate after it is in position in the body either by contact with or exposure to body fluids or based on an injection or other active introduction of a sterile liquid such as saline or water.

Figure 2:
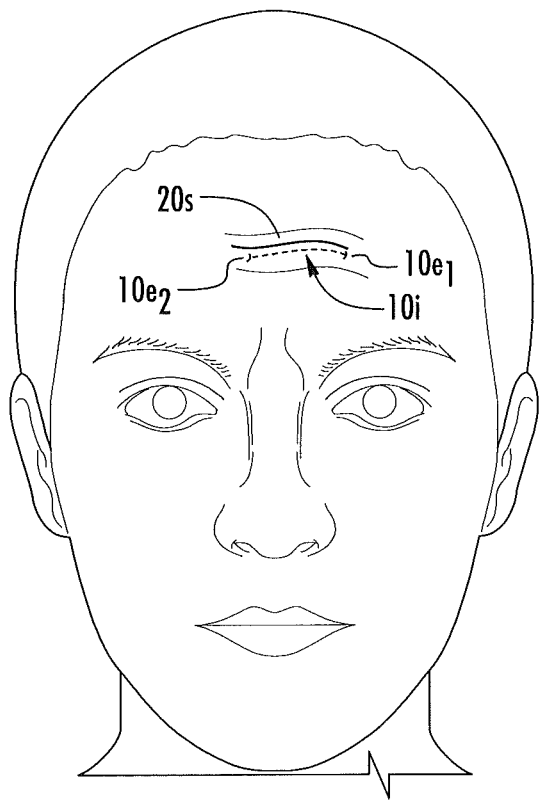
FIG. 2 is a schematic illustration of the thread of FIG. 1 in position.

FIG. 2 illustrates that the thread 10 can be left in position under the skin 20s and allowed to swell to fill the void and reduce or eliminate the wrinkle. The thread 10 can degrade and/or be resorbable over time in vivo and need not be removed from the body. The thread 10 may promote collagen growth at that site which may provide an improved rejuvenation effect with a longer term reduction in wrinkle formation/size. The thread 10 can be coated, sprayed, embedded or otherwise include one or more of: chemical collagen promoters such as cytokines and growth factors, antioxidants such as ascorbic acid, extracellular matrix macromolecules such as elastin, fibronectin and laminin and/or other therapeutics including anti-inflammatory agents, antibiotics and the like.

The thread 10, after partial and/or full hydration, can, in position, have a substantially resilient and laterally compressible configuration so that when skin is pressed down over the thread, a tactile soft touch, mimicking natural skin and underlying tissue, is provided. The thread 10 can be configured to substantially "rebound" to fill the void/wrinkle space after touch compression. The thread 10 can be configured to have "benign degradation", which means that the component degrades in the body without producing adverse or unnatural effects.

In some embodiments an external pad, such as an adhesively attachable (removable) silicone pad, may be placed over the implant site/thread 10 to facilitate a desired visual response. Heat, light or other supplemental therapies may also optionally be used.

The thread 10 can be attached to a needle 120 (similar to a suture needle) for placement of the thread under the skin, as shown in FIG. 1. The needle 120 can be straight or curved. The needle 120 can be a swaged needle or the needle may have an eye. In other embodiments, the end of the thread may be formed with a sharp tip using, for example, a coating to provide sufficient rigidity and sharpness suitable for insertion. In yet other embodiments, a collapsible thin-walled capsule device can be used to place the thread. See, e.g., co-pending U.S. patent application Ser. No. 13/105,353, the contents of which are hereby incorporated by reference as if recited in full herein. Alternatively, where the skin is open because of an injury or incision and the like, the thread(s) 10 can be positioned by directly placing the thread(s) on tissue under the skin without requiring any delivery device.

The thread 10 includes end portions $10e_1$, $10e_2$ that reside proximate the end of the treatment site (e.g., wrinkle). As shown in FIG. 2, the end portions $10e_1$, $10e_2$ may reside under the skin. Optionally, one or both end portions $10e_1$, $10e_2$ may be adhesively attached to local tissue (e.g., internally secured) so that the end portions are not externally visible. In other embodiments, one or both end portions $10e_1$, $10e_2$ may be externally visible at least for a short period of time after placement. Optionally, a small piece of tape, an adhesive applied to the skin, a knot in the thread, a clamp or external lock or other device or thread configuration may be used to secure one or both ends.

In some embodiments, it is contemplated that the externally visible portions may be removed (e.g., cut) or one or both ends may automatically retreat (the thread 10 may shrink in length as it swells in volume) under the skin after the thread swells sufficiently, e.g., about 15 minutes to 48 hours after insertion/placement.

In some embodiments, one end portion $10e_2$ may include a knot $10k$ that can be used during placement to inhibit sliding or lock the thread 10 into a desired position (FIG. 1).

In some embodiments, the thread 10 can be self-locking in position due to swelling after placement and/or otherwise be positioned without requiring any fixation means.

The collagen fiber thread 10 can be configured to swell, in situ, from a non-hydrated or partially hydrated state to a fully hydrated state, which may occur in about 10 minutes to about 48 hours, by at least about 30%. For gelatin fibers, the swelling can be even greater such as between about 2× (two times) to 21× (21 times greater), e.g., for 5% gelatin hydrogels, between about 7× to about 21× in weight. See, e.g., Koob et al., *Mechanical and thermal properties of novel polymerized NDGA-gelatin hydrogels*, Biomaterials 24 (2003), 185-1292, the contents of which are hereby incorporated by reference as if recited herein. The synthetic collagen fibers in the thread can be un-cross-linked, 1-ethyl-3-(3-dimethylaminopropyl)-carbodiimide (EDC) cross-linked, NDGA cross-linked or cross-linked with another biocompatible agent such as, for example, glutaraldehyde, formaldehyde, tannic acid, isocyanates, and epoxy resins. The thread 10 can include a combination of different types of synthetic collagen fibers 11.

Where the thread 10 includes one or more gelatin hydrogel fibers, the gelatin can be present in an amount between about 5-40% per swollen volume (in the dry state it is 100%); in an exemplary thread, gelatin can account for 2-50% of the dry weight of the thread.

The thread 10 can include a single collagen fiber 11. Alternatively, the thread 10 can be configured as a parallel array of snugly abutting synthetic collagen fibers 11, and/or a multi-fiber twisted or braided thread of synthetic collagen fibers 11. The thread 10 (and fiber or fibers) can have a substantially round or circular, elliptical or flat lateral cross-section. The synthetic collagen fiber(s) 11 in the thread 10 can have a length that is at least about 0.5 inches, typically at least about 1 inch, and more typically between about 1 inch to about 30 inches, such as between about 2-10 inches. The thread 10 can be cut to size before or after placement in the target site.

Figure 3:
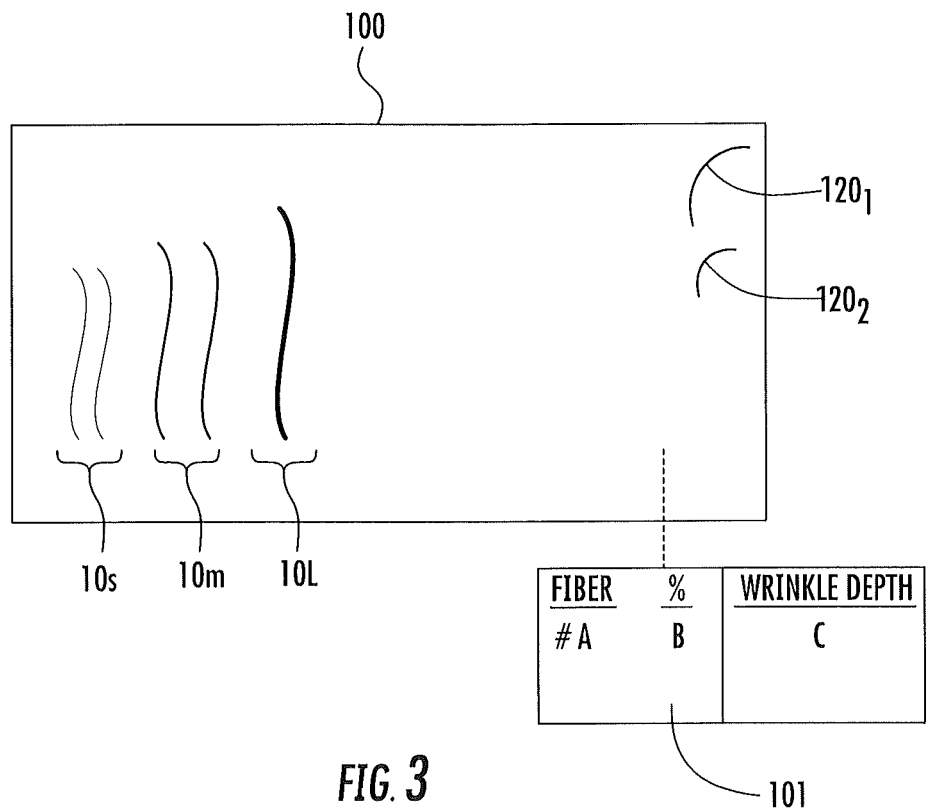
FIG. 3 is a schematic illustration of a medical kit according to embodiments of the present invention.
Figure 4:
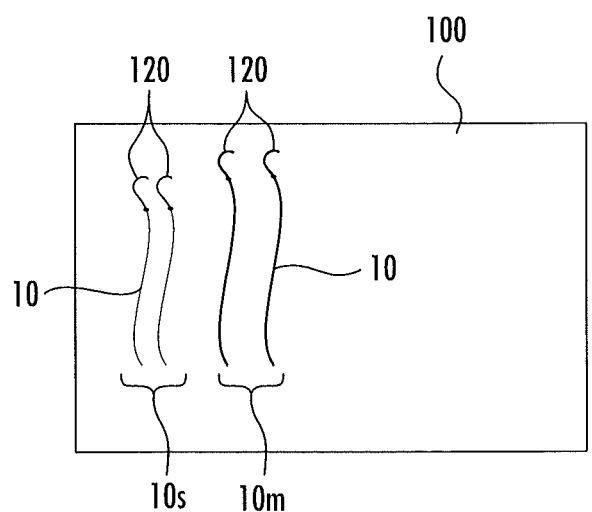
FIG. 4 is a schematic illustration of another example of a medical kit according to embodiments of the present invention.

The dry diameter of the thread 10 can vary in order to achieve the desired swelling volume; i.e., shallow wrinkles/small fiber 10s (FIGS. 3, 4), medium wrinkles/medium sized thread 10m (FIGS. 3, 4), and/or deep wrinkles/large fiber 10l (FIGS. 3, 4). The small thread/fibers 10s can have a dry diameter (average) of between about 0.1 mm to about 0.5 mm, the medium thread/fiber 10m can have a dry diameter (average) of between about 0.6-1 mm, while the large thread/fiber 10l can have a dry diameter of between about 1-2 mm. Other groupings of sizes may be used, e.g., only small and large or provided in even finer (smaller) size ranges, e.g., the threads 10 can be provided in five ranges (those discussed above with the size ranges further split to include extra small and extra large).

In some embodiments, the thread 10 can be provided as a single synthetic collagen fiber, typically ranging in size between about 0.1 mm to about 2 mm, dry, average.

In some embodiments, the thread 10 can be a single-fiber, porous collagen thread ranging in diameter from 0.2 mm to 2 mm.

The thread 10 can include a single cross-linked collagen gelatin (hydrogel) fiber. The diameter can vary as discussed above, for example, dry diameters from about 0.01 mm to about 2 mm, typically between about 0.1 mm to about 1 mm. Gelatin fibers will increase several fold in diameter, much more than synthetic collagen fibers as discussed above.

In other embodiments, the thread 10 can be a braided, twisted, or parallel array of a plurality of thin elongate collagen fibers 11, such as between about 0.01 to about 0.10 mm. The number of fibers selected and/or braid or twist pattern can correspond to a desired size of swollen volume. The number of fibers 11 in the thread 10 can range from, for example, between about 4 to about 100 fibers, typically between about 4 to about 20 collagen fibers. The braided/twisted and/or parallel array thread may have a substantially round cross-sectional shape. In other embodiments, the thread may be substantially flat.

As the thread 10 is intended for cosmetic use, it is not required to be load bearing, but typically is configured to have sufficient tensile strength to resist breaking or separating during placement (e.g., pulling into position using a needle 120, where this placement method is used).

As shown in FIGS. 3 and 4, the thread 10 can be provided in a sterile package 100p in a kit 100 with a selection of different size threads and/or thread types that can be matched to a treatment site, such as a shallow versus a deep wrinkle. The kit can optionally include one or more needles 120. FIG. 3 shows that the needles 120 may optionally be provided as separate components of the kit with the threads 10. The kit 10 may instead be provided with one size of thread. Different kits can include a respective different size thread or set of threads for treating cosmetic defects or wrinkles. Although shown as provided in three different size threads 10, 10s, 10m, 10l, two sizes or more than three sizes may also be used. The needle 120 can be provided pre-attached (e.g., swaged, pre-threaded in a kit 100 (FIG. 4) for use by a physician (FIG. 4).

To facilitate a clinician's selection of a proper size thread for a treatment site, a correlation/reference table 101 (FIG. 3) of size of a defect, void or wrinkle, to a recommended thread size can be provided. This reference table or chart can be provided with the kit (e.g., as a pamphlet, table or marking on a package providing the threads) and/or online or in a brochure as a look-up resource.

In some particular embodiments, the fibers can comprise NDGA-treated collagen. Suitable ways of forming NDGA polymerized and/or treated fibers are described in U.S. Pat. Nos. 6,565,960 and 6,821,530, the contents of which are hereby incorporated by reference as if recited in full herein. Generally stated, bulk collagen can be solubilized by digestion with a protease, then extruded into a synthetic fiber. Properly processed NDGA polymerized fibers are biocompatible. After the polymerization process, the fibers can be washed in ethanol and phosphate buffered saline to remove cytotoxins due to leachable reaction products. For additional discussion of the NDGA polymerized fibers, see, Thomas J. Koob, *Biomimetic approaches to Tendon Repair*, Comparative Biochemistry and Physiology Part A 133 (2002) 1171-1192. See also, co-pending U.S. Provisional Application Ser. No. 61/422,363, the contents of which are hereby incorporated by reference as if recited in full herein.

FIGS. 5A-5C are schematic illustrations of a series of steps that can be used to treat cosmetic defects. FIG. 5A shows an enlarged partial cross-section of skin 20s of a patient with a wrinkle 20w. FIG. 5B shows the thread 10 in a dry or partially hydrated state placed under the skin 20s in a void or valley 20v associated with a wrinkle 20w. FIG. 5C shows the thread 10 after hydration to an enlarged or swollen "equilibrium" hydrated state, which can fill the void 20v and/or push the epithelial or outer layer skin 20s outward. The thread 10 can thus reduce flaws or wrinkles, e.g., fill voids associated with wrinkles, scars or other externally visible flaws. For example, for wrinkle treatment, it is contemplated that an appropriately sized thread 10 can reduce wrinkle depth at least about 20%, about 30% and even about 50% or more.

FIG. 6A shows that a void filler or tissue expander 10f can be used to fill a void associated with excised, torn or otherwise missing or misshaped tissue or tissue has been removed by surgery or accident, for example. The void filler 10f is typically sized greater than a smaller "wrinkle" or small void-use threads. The void filler 10f can be provided as one or more components and can have any desired shape including a planar shape, an elliptical or oval cross-sectional shape or other desired shape having a suitable volume for the void. As shown, a flap of skin 20f can be sutured 105 on one or more sides or otherwise held in position over the void filler 10f. The void filler 10f can be placed in position before, during or after the flap of skin 20f is partially or totally attached.

As shown in FIG. 6B, the void filler 10f can be an implantable soft tissue medical void filler that is held in a sterile package 100. The void filler 10f can include at least one synthetic collagen fiber for implantation in a dry or partially hydrated state in the package, the at least one collagen fiber having a length that is at least about 0.25 inches. The void filler 10f can be flexible (resilient) and configured to reside under an outer skin layer to be able to lift the outer skin layer. The package 100 can include a use label 150 (typically on or in the package or in a box holding the package) identifying the content as a cosmetic soft tissue void filler that is particularly suitable for cosmetic and/or non-structural purposes.

Figure 7:
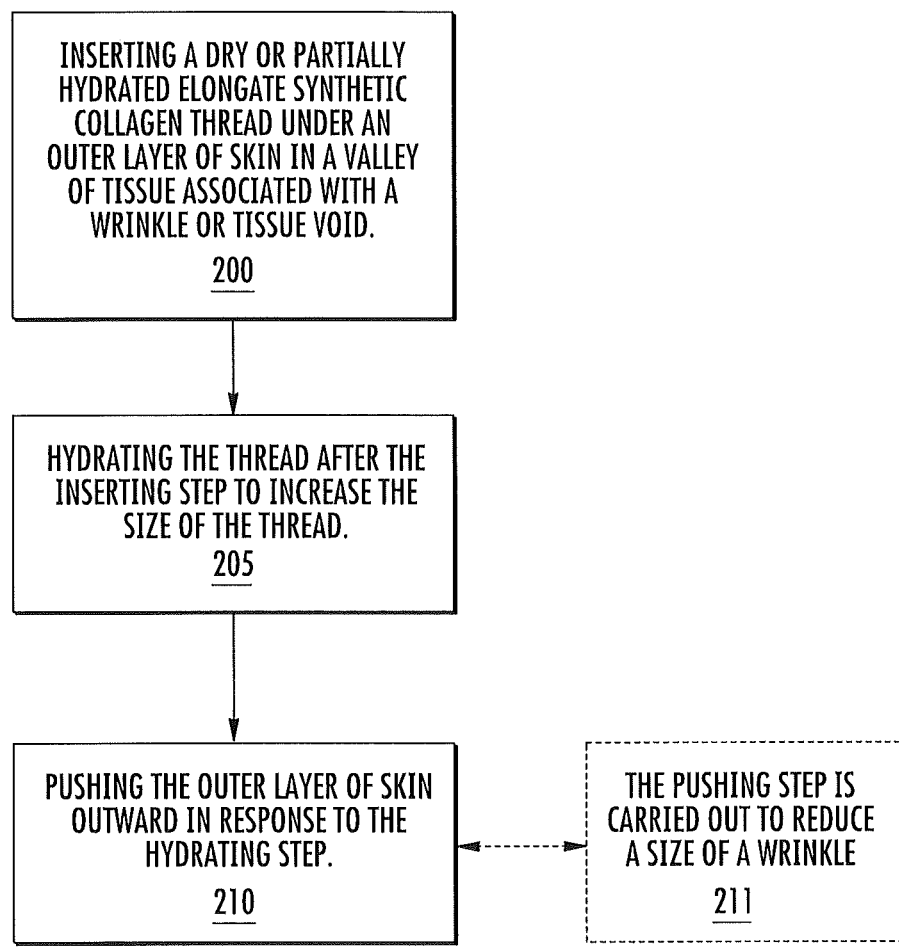
FIG. 7 is a flow chart of exemplary operations that can be used to carry out embodiments of the present invention.

FIG. 7 is a flow chart of exemplary methods that can be carried out according to embodiments of the present invention. A dry or partially hydrated elongate synthetic collagen thread can be inserted under an outer layer of skin in a valley of tissue associated with a wrinkle or other tissue void (block 200). The thread can be hydrated after the inserting step to increase size of the thread (block 205). The hydration can be based on exposure to body fluids in situ (e.g., "passive hydration"), or may be facilitated by active fluid introduction (e.g., "active hydration"). The size can be increased in cross-section by a desired amount, such as about 10-50% or other amount. The term "hydration" is used broadly and, if active hydration is used, then the liquid can include any suitable liquid and is not limited to water or saline or other water based solutions or liquids. The outer layer of skin can be pushed outward in response to the hydrating step (block 210). Optionally, the pushing step can be carried out to reduce the appearance of a wrinkle (block 211).

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. A cosmetic treatment kit, comprising:
    a plurality of discrete, separate threads of different diameters sized and configured for treating different size facial wrinkles, each thread is a single synthetic, elongate, continuous length collagen fiber in a dry or partially hydrated state, wherein the at least one synthetic, elongate, continuous length collagen fiber of each thread is configured to swell in situ in cross-sectional size at least about 30% after placement when fully hydrated, wherein, when fully hydrated, the discrete separate threads each have a resilient compressible configuration to thereby rebound after touch compression mimicking natural skin;
    a sterile package holding the plurality of discrete separate threads therein; and a correlation reference/table on or in the kit, wherein the correlation reference/table provides a size of a defect, void or wrinkle to a recommended thread size to thereby facilitate a clinician's selection of a proper size thread for a treatment site.

2. The kit of claim 1, wherein the kit comprises at least one needle sized and configured to insert a respective thread into tissue associated with a wrinkle, and wherein the respective threads are configured to swell when fully hydrated so that the outer layer of skin over the wrinkle is level with adjacent skin on each side of the wrinkle.

3. The kit of claim 1, wherein the threads are degradable or resorbable in vivo.

4. The kit of claim 1, wherein the at least one synthetic, elongate, continuous length collagen fiber of respective threads is a single synthetic collagen fiber and is un-crosslinked.

5. The kit of claim 1, wherein the at least one synthetic, elongate, continuous length collagen fiber of respective threads is a single synthetic collagen fiber and is crosslinked.

6. The kit of claim 1, wherein the threads are non load bearing, and wherein the threads comprise one or more of the following:
    a collagen promoter, antioxidant, extracellular matrix macromolecules, and an anti-inflammatory agent.

7. The kit of claim 1, wherein the synthetic, elongate, continuous length collagen fiber body of the threads are crosslinked with carbodiimide.

8. The kit of claim 1, wherein at least some of the threads comprise gelatin in an amount between about 5-40% per fully hydrated volume that occurs after placement in tissue.

9. A cosmetic treatment kit, comprising:
    a plurality of single-fiber threads of different diameters sized and configured to treat different size facial wrinkles, wherein the single fiber threads each are a single synthetic, elongate, continuous length collagen fiber body in a dry or partially hydrated state, wherein the single fiber threads are configured to swell in situ in cross-sectional size at least 30% after placement in tissue and when fully hydrated so that the outer layer of skin over the wrinkle is level with adjacent skin on each side of the wrinkle, and wherein the single-fiber threads each have a resilient compressible configuration when fully hydrated to thereby rebound after touch compression mimicking natural skin;
    a package holding the plurality of single-fiber threads in a sterile condition for surgical use; and a correlation reference/table in, on or appended to the kit, wherein the correlation reference/table provides a size of a defect, void or wrinkle to a recommended thread size to thereby facilitate a clinician's selection of a proper size thread for a treatment site.

10. The kit of claim 9, wherein the plurality of single fiber threads with the single synthetic, elongate, continuous length collagen fiber body are crosslinked with carbodiimide.

11. The kit of claim 9, wherein the plurality of the single-fiber threads comprise cytokines and/or growth factors.

12. The kit of claim 9, wherein the plurality of the single-fiber threads comprise antioxidants.

13. The kit of claim 9, wherein the plurality of the single-fiber threads comprise extracellular matrix macromolecules.

14. The kit of claim 9, wherein the plurality of the single-fiber threads comprise an anti-inflammatory agent.

15. The kit of claim 9, wherein at least some of the threads comprise gelatin in an amount between about 5-40% per fully hydrated volume.

16. A cosmetic treatment kit, comprising:
    a plurality of implantable cosmetic threads of different outer diameters, each cosmetic thread of the plurality of implantable cosmetic threads is a single synthetic, elongate, continuous length collagen fiber in a dry or partially hydrated state, wherein the plurality of cosmetic threads are sized to treat different size facial wrinkles, wherein the cosmetic threads swell in situ in cross-sectional size at least 30% after placement in tissue and when fully hydrated, wherein the cosmetic threads have a resilient compressible configuration when fully hydrated to thereby rebound after touch compression mimicking natural skin, and wherein at least some of the threads comprise gelatin in a range of 5-40% per volume when fully hydrated; and
    a package holding the plurality of implantable cosmetic threads in a sterile condition for surgical use.

17. A cosmetic treatment kit, comprising:
    a plurality of implantable cosmetic threads of different outer diameters, each cosmetic thread of the plurality of implantable cosmetic threads comprising at least one synthetic, elongate, continuous length collagen fiber in a dry or partially hydrated state, wherein the cosmetic threads are sized to treat different size facial wrinkles, wherein the cosmetic threads swell in situ in cross-sectional size at least 30% after placement in tissue and when fully hydrated, and wherein the cosmetic threads have a resilient compressible configuration when fully hydrated to thereby rebound after touch compression mimicking natural skin; and a package holding the plurality of implantable cosmetic threads in a sterile condition for surgical use, wherein at least some of the threads are a single synthetic, elongate continuous length collagen fiber.

\* \* \* \* \*